United States Patent
Nagai et al.

(10) Patent No.: US 10,508,383 B2
(45) Date of Patent: Dec. 17, 2019

(54) CLOTHING TREATMENT DEVICE

(71) Applicants: AQUA CO., LTD., Tokyo (JP);
Qingdao Haier Washing Machine Co., Ltd., Shandong (CN)

(72) Inventors: Takayuki Nagai, Tokyo (JP); Hazime Suzuki, Tokyo (JP); Tomohiro Yamauchi, Tokyo (JP); Katsuji Onishi, Tokyo (JP); Osamu Tanikoshi, Tokyo (JP)

(73) Assignees: Aqua Co., Ltd. (JP); Qingdao Haier Washing Machine Co., Ltd. (CN)

( * ) Notice: Subject to any disclaimer, the term of this patent is extended or adjusted under 35 U.S.C. 154(b) by 12 days.

(21) Appl. No.: 15/576,432

(22) PCT Filed: May 24, 2016

(86) PCT No.: PCT/CN2016/083137
§ 371 (c)(1),
(2) Date: Nov. 22, 2017

(87) PCT Pub. No.: WO2016/188404
PCT Pub. Date: Dec. 1, 2016

(65) Prior Publication Data
US 2018/0155865 A1    Jun. 7, 2018

(30) Foreign Application Priority Data

May 27, 2015    (JP) .................................. 2015-107888

(51) Int. Cl.
*D06F 58/20*    (2006.01)
*D06F 58/14*    (2006.01)
(Continued)

(52) U.S. Cl.
CPC ............. *D06F 58/203* (2013.01); *A61L 2/202* (2013.01); *A61L 9/122* (2013.01); *D06F 58/14* (2013.01);
(Continued)

(58) Field of Classification Search
CPC ........ D06F 58/14; D06F 58/203; A61L 2/202; A61L 9/122; A61L 2202/26; A61L 2209/212
See application file for complete search history.

(56) References Cited

U.S. PATENT DOCUMENTS 5,815,961 A * 10/1998 Estes ....................... D06F 71/16
38/14
6,134,806 A    10/2000 Dhaemers
(Continued)

FOREIGN PATENT DOCUMENTS

CN    1170061 A    1/1998
CN    202989621 U    6/2013
(Continued)

OTHER PUBLICATIONS

European Search Report dated Nov. 29, 2018, for Application No. 16799292.4.

*Primary Examiner* — Benjamin L Osterhout
(74) *Attorney, Agent, or Firm* — Burns & Levinson LLP; Joseph M. Maraia

(57) ABSTRACT

Disclosed is disclosure clothing treatment device capable of effectively preventing odour from reabsorbing to clothing. A clothing deodorizing device includes: a bag body for accommodating clothing; an ozone supply apparatus including an ozone generator and a blowing fan wherein the air supply fan operates to deliver the ozone generated by the ozone generator into the bag body by virtue of the flow of the air; and a control part for controlling operation of the ozone generator and the blowing fan. After performing deodoriza-
(Continued)

tion operation that enables the ozone generator and the blowing fan to operate, the control part performs reabsorption preventing operation that enables the blowing fan to operate intermittently.

7 Claims, 15 Drawing Sheets

(51) Int. Cl.
    *A61L 2/20*     (2006.01)
    *A61L 9/12*     (2006.01)

(52) U.S. Cl.
    CPC ..... *A61L 2202/26* (2013.01); *A61L 2209/212* (2013.01)

(56) References Cited

U.S. PATENT DOCUMENTS

| | | | | |
|---|---|---|---|---|
| 6,425,192 | B2* | 7/2002 | Arrieta | D06F 73/02 34/202 |
| 6,427,365 | B2* | 8/2002 | MacGregor | D06F 73/02 38/1 A |
| 6,622,529 | B1* | 9/2003 | Crane | D06F 43/00 68/5 C |
| 7,060,106 | B2* | 6/2006 | Kleker | D06F 17/04 68/205 R |
| 8,038,963 | B1* | 10/2011 | Chen | A61L 2/202 34/210 |
| 8,151,495 | B2* | 4/2012 | Kim | D06F 73/02 38/1 A |
| 8,656,744 | B2* | 2/2014 | Kim | D06F 35/00 422/24 |
| 9,096,969 | B2* | 8/2015 | Moon | D06F 58/203 |
| 2006/0096331 | A1* | 5/2006 | Kim | A61L 2/14 68/5 C |
| 2007/0166186 | A1* | 7/2007 | Stec | A01M 31/00 422/5 |
| 2010/0281924 | A1 | 11/2010 | Tobi et al. | |
| 2011/0268625 | A1 | 11/2011 | Chen | |
| 2012/0159802 | A1 | 6/2012 | Seiffert et al. | |

FOREIGN PATENT DOCUMENTS

| | | |
|---|---|---|
| DE | 202009007256 U1 | 9/2009 |
| JP | 3142564 U | 6/2008 |
| KR | 10-2007-0053046 | 5/2007 |

\* cited by examiner

CLOTHING TREATMENT DEVICE

CROSS REFERENCE TO RELATED APPLICATIONS

This application is the U.S. national phase entry under 35 U.S.C. § 371 of International Application No. PCT/CN2016/083137, filed May 24, 2016, entitled CLOTHING TREATMENT DEVICE, which claims priority to Japanese Patent Application No. 2015-107888, filed May 27, 2015, the contents of which are incorporated herein by reference in their entirety for all purposes.

TECHNICAL FIELD

The present disclosure relates to a clothing treatment device for implementing treatment, such as deodorization, on clothing.

BACKGROUND

A clothing renovating apparatus is known. The clothing renovating apparatus includes a storage container capable of hanging clothing on a hanging rod for storage. The clothing renovating apparatus enables high-temperature and high-humidity air to circulate inside the storage container, and then introduces circulating air absorbing clothing odour into an ozone deodorizer, thereby deodorizing the clothing (Refer to patent document 1).

Since the clothing renovating apparatus includes the storage container, a body of the apparatus is easy to become larger. Therefore, a clothing treatment device, which is easy to install at home without large installation space, includes a bag body for accommodating clothing and an ozone supply apparatus for supplying air containing ozone into the bag body, and can implementing treatment, such as deodorization, on clothing accommodated in the bag body through ozone, is considered to be realized.

Existing Technical Literature

Patent Document

Patent Literature 1: Japan Patent Publication No. 04-327900

Problems to be Solved by the Disclosure

In the clothing treatment device described above, under a condition that odour ingredients not completely decomposed in a deodorization operation process are retained in the air in the bag body at the end of deodorization operated through the ozone, during a period from the end of the deodorization operation to the removal of the clothing from the bag body, odour may be reabsorbed to the clothing.

SUMMARY

In view of the problem, a technical solution of the present disclosure is completed. A object of the present disclosure is to provide a clothing treatment device capable of effectively preventing odour from reabsorbing to clothing.

Solution for Solving the Problems

A clothing treatment device according to a main embodiment of the present disclosure includes: a bag body for accommodating clothing; an ozone supply part including an ozone generator and a blowing fan, wherein the blowing fan operates to deliver ozone generated by the ozone generator into the bag body by virtue of flow of air; and a control part for controlling operation of the ozone generator and the blowing fan. After performing a first operation which enables the ozone generator and the blowing fan to operate, the control part performs a second operation which enables the blowing fan to operate intermittently.

Through the above structure, since second operation is performed after the end of clothing deodorization performed through first operation, and flow of air is generated within the bag body until the clothing are taken from the bag body, the odour can be prevented from reabsorbing to the clothing inside the bag body. Moreover, since the blowing fan is operated intermittently in the second operation, the bag body is repeatedly expanded and contracted. Thus, through expansion and contraction in the bag body, the air not only flows to an outlet direction from an inlet of the bag body, but also flows to other directions. Therefore, the odour ingredients can be effectively away from the clothing inside the bag body.

Further, through the above structure, since the bag body is repeatedly expanded and contracted during the second operation, a user can know that the first operation has been ended according to a tendency of the bag body distinctive from a tendency during the first operation.

Further, through the above structure, since the blowing fan is operated intermittently in the second operation, power consumption can be reduced compared with a condition of continuous operation of the blowing fan.

The clothing treatment device in the present embodiment can adopt a structure that further includes a detection part for detecting whether a clothing throwing inlet of disposed at the bag body is opened. In this case, the control part ends the second operation under a condition that the second operation is performed for a specified time and the detection part detects that the throwing inlet is opened before the specified time expires.

Through the above structure, the second operation after the clothing is taken from the bag body can be prevented, and power waste can be prevented.

The clothing treatment device in the present embodiment can adopt a structure that further includes an operation part capable of selecting operation time of the first operation from a first time and a second time longer than the first time. In this case, the control part performs the second operation after the first operation is performed for the first time, and does not perform the second operation after the first operation is performed for the second time.

Through the above structure, since the second operation is not performed under a condition that the odour ingredients are considered to hardly remain after deodorization operation is performed for a longer time, power waste can be prevented.

The clothing treatment device in the present embodiment can adopt such a structure that the control part starts the second operation after a specified waiting time from an end of the first operation.

Through the above structure, since during the waiting time expires the bag body is contracted to return to a state before the first operation, the user can be notified that the first operation is ended through the state of the bag body before the second operation is started.

Effects of the disclosure

Through the present disclosure, a clothing treatment device can be provided, capable of effectively preventing the odour from reabsorbing to the clothing.

Effects and significance of the present disclosure can be further clarified by describing embodiments shown below. However, the following embodiments are just illustration during implementation of the present disclosure. The present disclosure is not limited by disclosure in the following embodiments.

LIST OF REFERENCE NUMERALS

10: bag body; 11: throwing inlet; 20: ozone supply apparatus (ozone supply part); 450: operation part; 470: lock detection part (detection part); 600: ozone generator; 700: blowing fan; and 910: control part.

DETAILED DESCRIPTION

An embodiment of a clothing treatment device according to the present disclosure, i.e., a clothing deodorizing device, is described below with reference to drawings.

Figure 1:
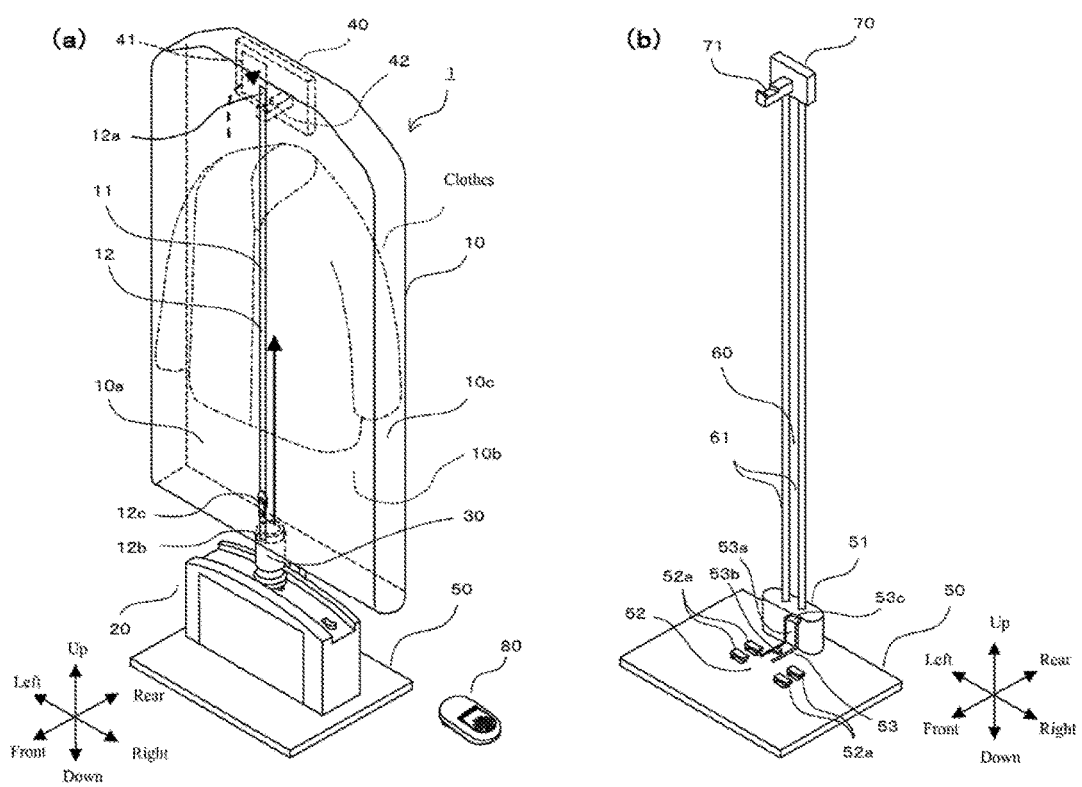
FIG. 1 is a structural diagram illustrating a clothing deodorizing device according to embodiments.
Figure 2:
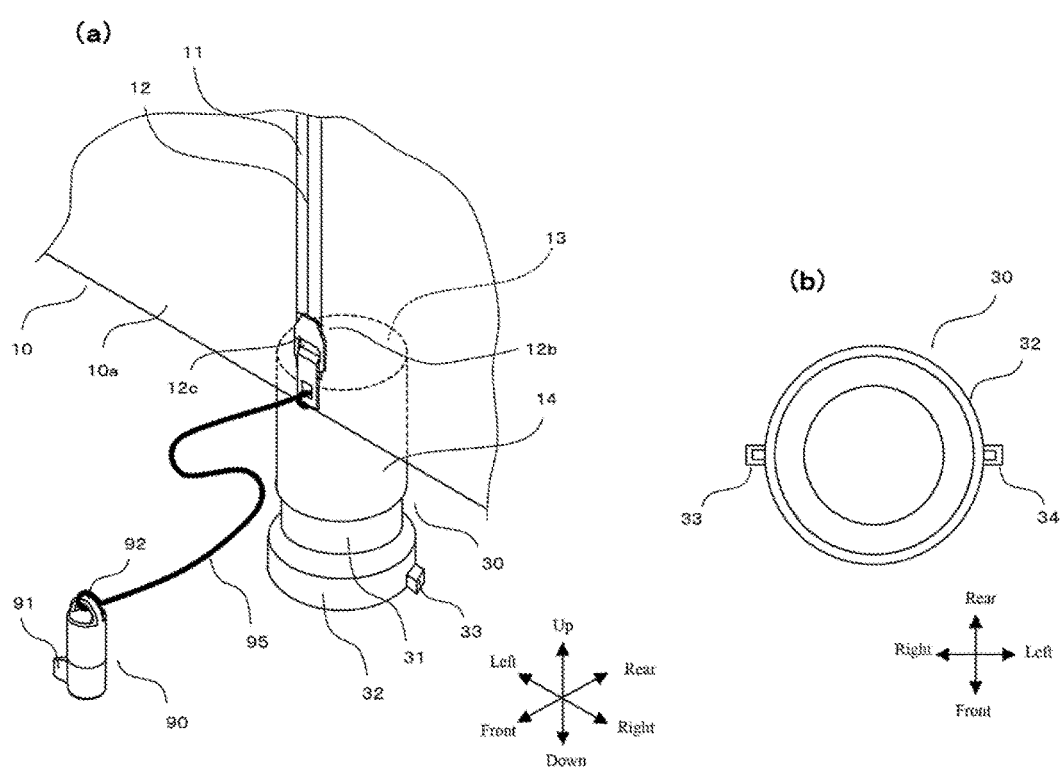
FIG. 2 is a structural diagram illustrating a bag body, an induction pipe and a detection lock according to embodiments.
Figure 3:
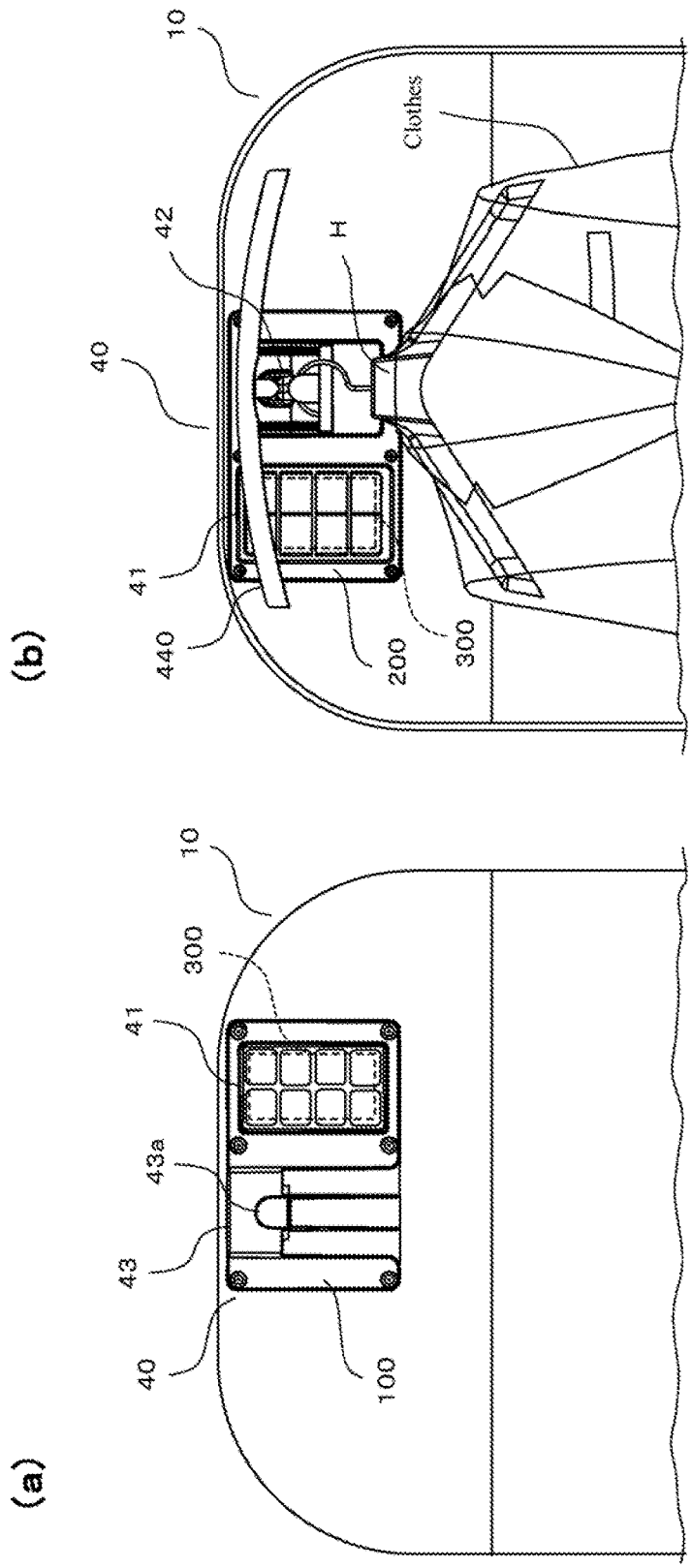
FIG. 3 is a structural diagram illustrating an exhaust and clothes hanger holding unit according to embodiments.
Figure 4:
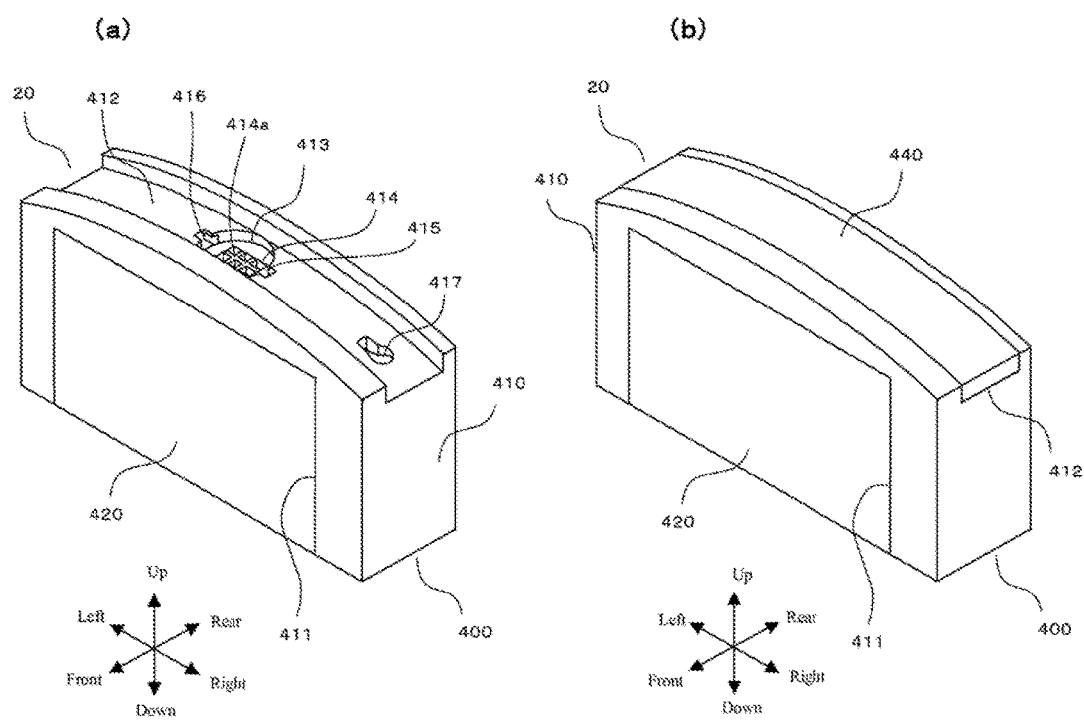
FIG. 4 is a structural diagram illustrating an ozone supply apparatus according to embodiments.
Figure 5:
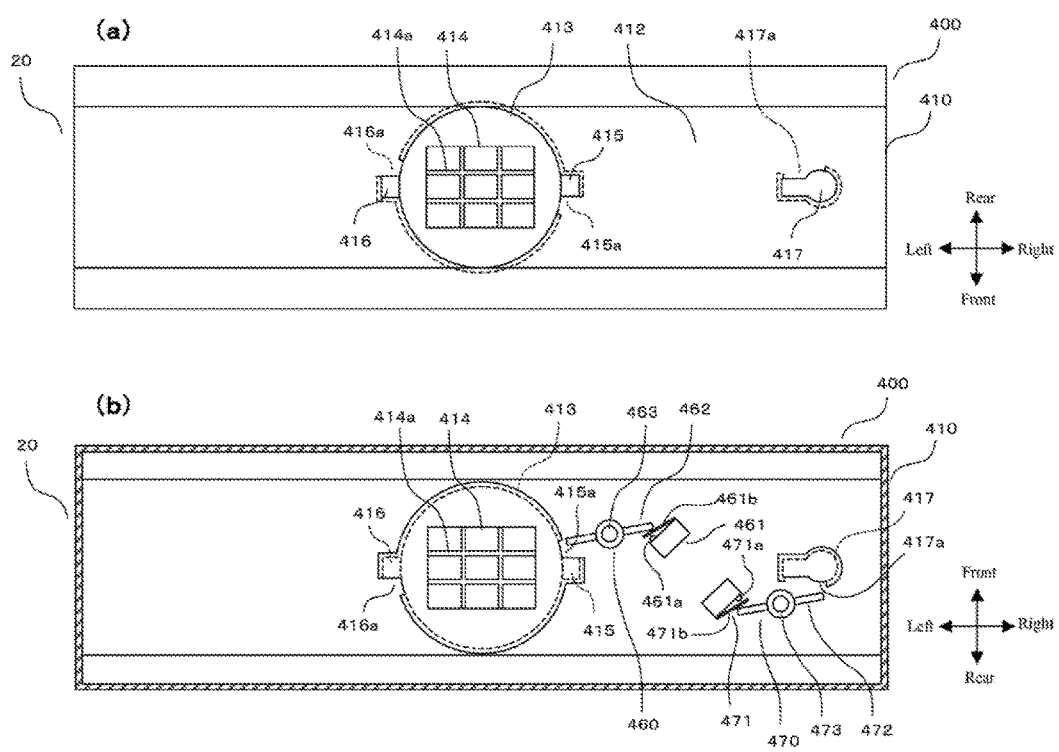
FIG. 5 is a structural diagram illustrating an ozone supply apparatus according to embodiments.
Figure 6:
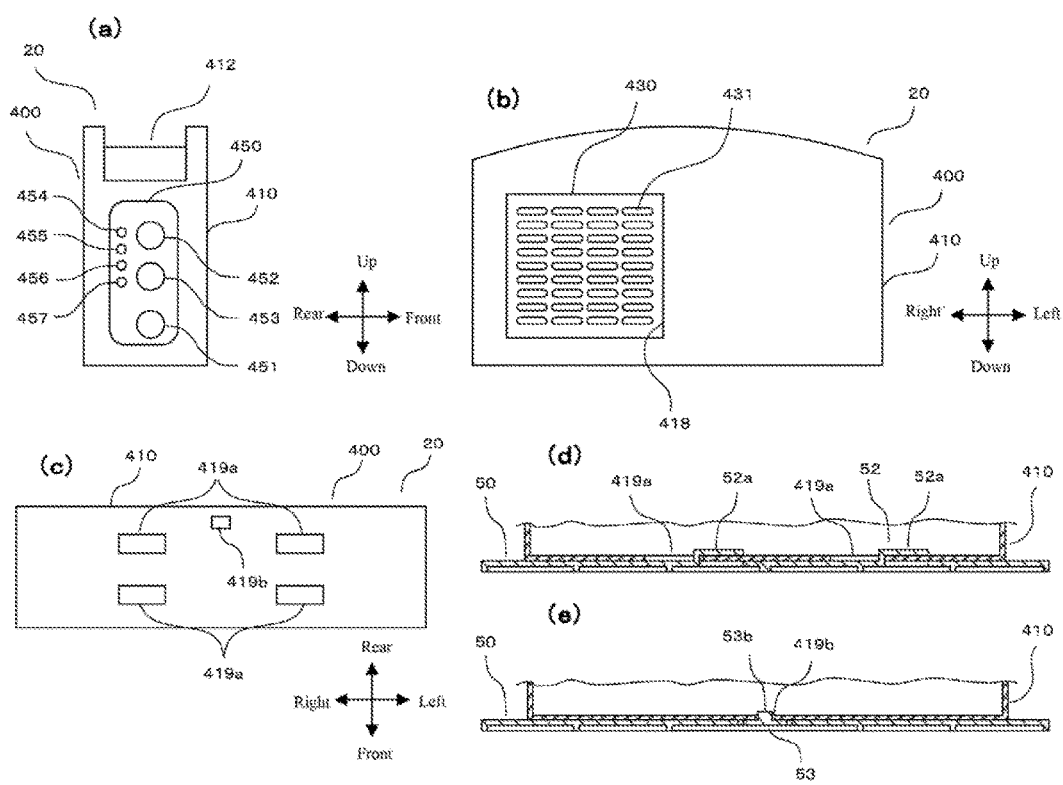
FIG. 6 is a structural diagram illustrating an ozone supply apparatus according to embodiments.
Figure 7:
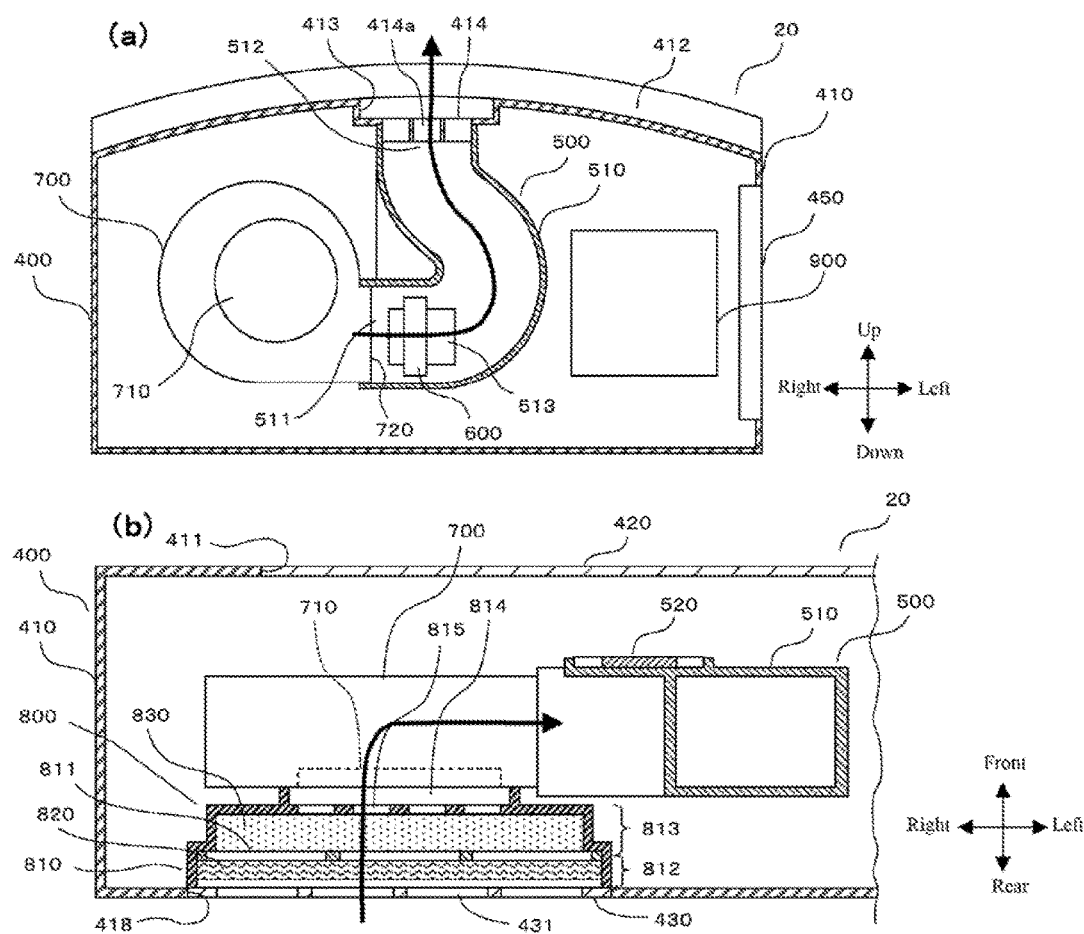
FIG. 7 is a structural diagram illustrating an ozone supply apparatus according to embodiments.

FIG. 1 is a structural diagram illustrating a clothing deodorizing device 1. FIG. 1(a) is a perspective diagram illustrating a clothing deodorizing device 1. FIG. 1(b) is a perspective diagram illustrating a base 50, a supporting column 60 and a bag body holding part 70 that form a clothing deodorizing device 1. In addition, FIG. 2 is a structural diagram illustrating a bag body 10, an induction pipe 30 and a detection lock 90. FIG. 2(a) is a perspective diagram illustrating a lower central part of a bag body 10. FIG. 2(b) is a bottom view illustrating an induction pipe 30. Moreover, FIG. 3 is a structural diagram illustrating an exhaust and clothes hanger holding unit 40. FIGS. 3(a) and (b) are respectively a rear view and a front view illustrating an upper part of a bag body 10 provided with an exhaust and clothes hanger holding unit 40. It should be noted that a front surface of the bag body 10 is not shown in FIG. 3(b).

By referring to FIG. 1 to FIG. 3, the clothing deodorizing device 1 includes: the bag body 10, an ozone supply apparatus 20, an induction pope 30, an exhaust and clothes hanger holding unit 40, a base 50, a supporting column 60, a bag body holding part 70 and a fragrance supply unit 80.

The bag body 10 accommodates various clothing such as western-style clothing and coats. The bag body 10 is formed in a manner of overlapping a plurality of airtight fabrics, providing an adequate tightness. The bag body 10 has an approximately lengthwise cuboid compressed from front to rear, and is dimensioned up-down to be capable of accommodating long clothing such as long shirts and long coats. In addition, the bag body 10 is dimensioned front-rear to be capable of accommodating one piece of clothing. It should be noted that the bag body 10 can also be dimensioned up-down to be incapable of accommodating long clothing, and be dimensioned front-rear to be capable of accommodating about two or three pieces of clothing arranged from front to rear.

On a front surface of the bag body 10, a gap that forms a throwing inlet of the clothing is formed from an upper end to a lower end in an approximate center of a left-right direction. A zipper 12 is installed at the throwing inlet 11. A starting end part 12a and an end part 12b when the zipper 12 performs locking are respectively located on an upper end and a lower end of the bag body 10. A slider 12c of the zipper 12 moves between the starting end part 12a and the end part 12b. When the slider 12c is pulled downwards from the starting end part 12a, the zipper 12 is closed so that the throwing inlet 11 is locked. When the slider 12c is pulled upwards from the end part 12b, the zipper 12 is opened so that the throwing inlet 11 is opened.

As shown in FIG. 2(a), the detection lock 90 is connected with the slider 12c, and more specifically with a handle of the slider 12c through a connecting rope 95. The detection lock 90 is used for detecting locking of the throwing inlet 11 by the zipper 12. The detection lock 90 has a cylindrical shape. A protruding part 91 is formed at a lower end part of a circumferential surface of the detection lock 90, and a hanging ring part 92 for fixing the connecting rope 95 is formed at an upper end part. One end part of the connecting rope 95 is connected with the handle of the slider 12c, and the other end part thereof is connected with the hanging ring part 92. The connecting rope 95 may be a rope with a predetermined length, for example, a silk ribbon, a chain and a metal wire.

The ozone supply apparatus 20 performs deodorization operation for deodorizing the clothing and fragrance increasing operation for increasing fragrance on the clothing. During deodorization operation, the ozone supply apparatus 20 supply air containing the ozone to the bag body 10 by an operation of providing the exhausted air containing the ozone. In addition, when fragrance increasing operation, the ozone supply apparatus 20 supply air without the ozone to the bag body 10 by an operation of providing the exhausted air without the ozone. The ozone supply apparatus 20 is equivalent to an ozone supply part of the present disclosure.

The induction pipe 30 is connected with the bag body 10 and the ozone supply apparatus 20, and is used for leading the air exhausted from the ozone supply apparatus into the bag body 10. As shown in FIG. 2, an air inlet 13 is disposed in a central part at the lower of the bag body 10. A front end part of the induction pipe 30 is fixed to a cylindrical part 14 which droops from the inlet 13. The induction pipe 30 includes a cylindrical main part 31 with a relatively small outer diameter and a cylindrical connecting part 32 formed under the main part 31 and having a relatively large outer diameter. A right claw part 33 and a left claw part 34 are formed at a lower end of the connecting part 32 and respectively face a right and left sides of the bag body 10 in a state of installation on the bag body 10.

An exhaust and clothes hanger holding unit 40 is disposed on an upper part of a rear surface of the bag body 10. As shown in FIG. 3, the exhaust and clothes hanger holding unit 40 includes an exhaust part 41, a clothes hanger holding part 42 and an installation part 43. The exhaust and clothes hanger holding unit 40 includes a rear unit 100 and a front unit 200 connected in a manner of clamping the upper part of the rear surface of the bag body 10 from an outer and inner sides.

The air from the bag body 10 is exhausted to the outside through the exhaust part 41. An ozone removing filter 300 is installed on the exhaust part 41. The ozone removing filter 300 uses, for example, an activated carbon/catalyst filter formed by transferring activated carbon and a catalyst to base material such as aluminum. The ozone removing filter 300 removes the ozone contained in the air through the exhaust part 41. The clothes hanger holding part 42 retains and hangs a clothes hanger H for clothing. In addition, the clothes hanger retention part 42 retains an upper cover 440 formed into a lalongate platy shape slightly bent into an arch. The upper surface of the bag body 10 is strengthened at an inner side through the upper cover 440. The installation part 43 is formed into a quadrangular box shape extending rearwards, and an installation hole 43a is formed in a rear surface of the installation part 43.

The base 50 is a flat plate with a specified shape, such as a quadrangle. The ozone supply apparatus 20 is disposed above the base 50. A supporting part 51 for supporting the supporting column 60 is formed at a rear of the base 50. Moreover, a first fixing part 52 and a second fixing part 53 are disposed at the base 50 for fixing the ozone supply apparatus 20 by facing the front surface of the ozone supply apparatus 20 toward a direction of the front surface of the base 50. The first fixing part 52 includes a plurality of hooked claw parts 52a. The second fixing part 53 includes: an L-shaped elastic rod 53a with one end part supported by the base 50, a bulge 53b disposed at the rear slightly relative to one end part of the elastic rod 53a, and a pressing part 53c disposed on the other end part of the elastic rod 53a. When the pressing part 53c is pressed downwards, the elastic rod 53a deforms elastically and the bulge 53b is withdrawn into the lower part.

The supporting column 60 includes two rods 61. A lower end part of the supporting column 60 is installed on the supporting part 51, and stands upright relative to the base 50. The supporting column 60 may not include two rods 61, but includes one or more than three rods. In addition, a telescopic mechanism capable of adjusting the height of the supporting column 60 can also be disposed on the supporting column 60.

A bag body holding part 70 is installed at an upper end of the supporting column 60. The bag body holding part 70 has a holding part 71 protruding forwards. By inserting the holding part 71 into the installation hole 43a of the installation part 43, the bag body 10 can be hanged and retained without moving in any direction of front and rear, up and down and left and right.

The fragrance supply unit 80 is used when fragrance increasing operation is performed through the ozone supply apparatus 20. The fragrance supply unit 80 is detachably installed to the induction pipe 30, so that air supplied to the bag body 10 contains fragrant ingredients.

Next, a detailed structure of the ozone supply apparatus 20 is described.

FIGS. 4 to 7 are structural diagrams illustrating an ozone supply apparatus 20. FIG. 4(a) is a perspective diagram illustrating an ozone supply apparatus 20 without an upper cover 440. FIG. 4(b) is a perspective diagram illustrating an ozone supply apparatus 20 with an upper cover 440. FIG. 5(a) is a top view illustrating an ozone supply apparatus 20. FIG. 5(b) is a transverse section view of an upper surface of a shell 400 of an ozone supply apparatus 20 viewed from an inner side. FIGS. 6(a) to (c) are a left view, a rear view and a bottom view illustrating an ozone supply apparatus 20. FIGS. 6(d) and (e) are side section views illustrating a main part of an ozone supply apparatus 20 in a state of being fixed to the base 50. FIG. 7(a) is a longitudinal section view illustrating an ozone supply apparatus 20 viewed from a rear surface. FIG. 7(b) is a transverse section view illustrating a main part of an ozone supply apparatus 20 viewed from an upper side. It should be noted that a right inserting concave part 415, a left inserting concave part 416, a lock inserting concave part 417, a pipe detection part 460 and a lock detection part 470 are not shown in FIG. 7(a).

The ozone supply apparatus 20 includes a shell 400, a vent pipe 500, an ozone generator 600, a blowing fan 700, an air suction unit 800 and a control unit 900.

The shell 400 includes: a shell body 410, a front cover 420, an air suction hood 430, an upper cover 440 and an operation part 450. As shown in FIG. 4(a), the shell body 410 has a lalongate rectangular shape with an upper surface gently bent. A front surface opening part 411 is formed on a front surface of the shell body 410, and is detachable closed through the front cover 420.

On the upper surface of the shell body 410, a concave part 412 is configured to be a concave shape identical with a shape of the upper cover 440. In the center of the concave part 412, an inserting port part 413 is configured to be a concave circular shape. An exhaust port 414 with a latticed rectification rib 414a is disposed at the inserting port part 413. At the concave part 412, a right inserting concave part 415 and a left inserting concave part 416 with shapes corresponding to the right claw part 33 and the left claw part 34 of the induction pipe 30 are formed on the left side and the right side of the inserting port part 413. As shown in FIGS. 5(a) and (b), at a front side of the right inserting concave part 415, a right opening part 415a is configured in such a manner that the right claw part 33 inserted into the right inserting concave part 415 only turns right to move by about an amount of distance of one right claw part 33. Similarly, at a rear side of the left inserting concave part 416, a left opening part 416a is configured in such a manner that the left claw part 34 inserted into the left inserting concave part 416 only turns right to move by about an amount of distance of one left claw part 34.

At the concave part 412, the lock inserting concave part 417 with a shape corresponding to the detection lock 90 is disposed at a right end part. As shown in FIGS. 5(a) and (b), an opening part 417a is disposed at a side surface of the lock inserting concave part 417 at the rear side.

As shown in FIG. 4(b), when the clothing deodorizing device 1 is not used, the upper cover 440 removed from the bag body 10 can be installed on the concave part 412. Thus, since a storage site of the upper cover 440 removed from the bag body 10 is ensured, the upper cover 440 can be prevented from being lost when not used. In addition, dust can be prevented from entering the shell 400 from the exhaust port 414 and the lock inserting concave part 417 when the clothing deodorizing device is not used.

As shown in FIG. 5(b), the pipe detection part 460 and the lock detection part 470 are configured at an inner side of the upper surface of the shell body 410. The pipe detection part 460 includes a detection switch 461 and a relay rod 462. The detection switch 461 has a switch part 461a and a rod part 461b for pressing the switch part 461a. The relay rod 462 is installed in a free rotation mode on a rotating shaft 463 formed at the inner side of the upper surface of the shell body 410. One end of the relay rod 462 is located near the right inserting concave part 415, and the other end comes into contact with the detection switch 461. The lock detection part 470 includes a detection switch 471 and a relay rod 472. The detection switch 471 has a switch part 471a and a rod part 471b for pressing the switch part 471a. The relay rod 472 is installed in a free rotation mode on a rotating shaft 473 formed at the inner side of the upper surface of the shell body 410. One end of the relay rod 472 is located near the lock inserting concave part 417, and the other end comes into contact with the detection switch 471. The lock detection part 470 is equivalent to the detection part of the present disclosure.

As shown in FIG. 6(a), the operation part 450 is arranged on a left side surface of the shell body 410. The operation part 450 includes a power button 451, a deodorization button 452, a fragrance increasing button 453 and a selection button 454. The power button 451 is used for switching on and switching off a power supply of the clothing deodorizing device 1. The deodorization button 452 is used for starting deodorization operation. The fragrance increasing button 453 is used for starting fragrance increasing operation. The selection button 454 is used for selecting operation times of the deodorization operation and the fragrance increasing operation from "0.5 hour", "2 hours", "4 hours" and "8 hours". "0.5 hour", "2 hours" and "4 hours" are equivalent to the first time of the present disclosure, and "8 hours" is equivalent to the second time of the present disclosure. It should be noted that the selected time may be not limited to the above four times, and additionally, each time can also be not limited to the above four values.

In addition, the operation part 450 includes a non-piping informing part 455, a throwing inlet opening informing part 456, an operation time informing part 457 and an operation prevention informing part 458. The non-piping informing part 455 is, for example, formed by LED, and is used for informing that the induction pipe 30 is not connected with the ozone supply apparatus 20 by lighting. The throwing inlet opening informing part 456 is, for example, formed by LED, and is used for informing that the throwing inlet 11 of the bag body 10 is not locked by lighting. The operation time informing part 457 has four time informing parts corresponding to each operation time selected through the selection button 454, such as four LEDs. The selected operation time is informed through flashing of the time informing part corresponding to the operation time. The operation prevention informing part 458 is, for example, formed by LED, and reabsorption preventing operation for preventing the smell from reabsorbing to the clothing is informed through flashing.

As shown in FIG. 6(b), an air suction port 418 is formed in a rear surface of the shell body 410, and is detachably closed through the air suction hood 430. A plurality of air suction holes 431 are formed in the air suction hood 430.

As shown in FIG. 6(c), at a bottom surface of the shell body 410, a first installation hole 419a is formed corresponding to each claw part 52a of the first fixing part 52 of the base 50. A second installation hole 419b is formed corresponding to the bulge 53b of the second fixing part 53. When a user presses the pressing part 53c of the second fixing part 53 downwards to withdraw the bulge 53b, the claw part 52a pass through the first installation hole 419a to load the ozone supply apparatus 20 on the base 50 such that the ozone supply apparatus 20 transversely slides, as shown in FIG. 6(d), to clamp the claw part 52a with a bottom surface of the shell body 410. Then, when the user stops pressing the pressing part 53c, as shown in FIG. 6(e), the bulge 53b is embedded into the second installation hole 419b. Thus, the ozone supply apparatus 20 is fixed to the base 50 without moving in directions of up and down, front and rear and left and right. Therefore, the ozone supply apparatus 20 can be prevented from falling due to a force applied to the ozone supply apparatus 20 when the bag body 10 is inflated because of the air supplied by the ozone supply apparatus 20.

A vent pipe 500, an ozone generator 600, a blowing fan 700, an air suction unit 800 and a control unit 900 are configured inside the shell 400.

As shown in FIGS. 7(a) and (b), the vent pipe 500 includes a pipe body 510 and a pipe cover 520. An induction port 511 of the pipe body 510 is connected with the exhaust port 720 of the blowing fan 700, and an eduction port 512 of the pipe body 510 is connected with the exhaust port 414. The ozone generator 600 is disposed near the induction port 511 inside the pipe body 510. The pipe body 510 is configured in such a shape that the pipe body 510 extends from the induction port 511 to the left and goes back to the right over the configuration position of the ozone generator 600, and then extends upwards to the eduction port 512. That is, a part of a downstream side of the pipe body 510 forming the ozone generator 600 is configured to be an S shape.

The ozone generator 600 is a discharge type ozone generator. Discharge such as corona discharge, silent discharge is generated between a pair of electrodes, and ozone is generated through the air between a pair of electrodes. At a front surface of the pipe body 510, an opening part 513 is formed in a position corresponding to the ozone generator 600. The opening part 513 is closed through the pipe cover 520. The user can remove the front cover 420 and the pipe cover 520, so as to clean the electrodes through the opening part 513 to maintain the ozone generator 600.

The blowing fan 700 is a centrifugal fan. A suction inlet 710 is disposed in a side surface of the blowing fan 700, and an exhaust port 720 is disposed in a circumferential surface of the blowing fan 700. The suction inlet 710 is opposite to the air suction port 418 on the rear surface of the shell 400. The blowing fan 700 obtains the air from the suction inlet 710, and delivers the obtained air to the ozone generator 600 inside the vent pipe 500. The blowing fan 700 can also use other fans besides the centrifugal fan, such as an axial flow fan.

As shown in FIG. 7(b), an air suction unit 800 is disposed between the air suction port 418 of the shell 400 and the suction inlet 710 of the blowing fan 700. The air suction unit 800 includes an air suction pipe 810, a dust filter 820 and an ozone removing filter 830.

The air suction pipe 810 is divided into a first filter accommodating part 812 at a side of the air suction port 418 and a second filter accommodating part 813 at a side of the blowing fan 700 through a latticed dividing plate 811. The dust filter 820 is accommodated at the first filter accommodating part 812, and the ozone removing filter 830 is accommodated at the second filter accommodating part 813. The dust filter 820 removes dust included in the air obtained from the air suction port 418. The ozone removing filter 830 removes the ozone included in the air passing through the dust filter 820. The ozone removing filter 830, identical with the ozone removing filter 300 of the exhaust and clothes hanger holding unit 40, can use activated carbon/catalyst filter.

A connecting part 814 is disposed at the air suction pipe 810 for connecting with the suction inlet 710 of the blowing fan 700, and is communicated with the second filter accommodating part 813 through a communication hole 815.

Figure 8:
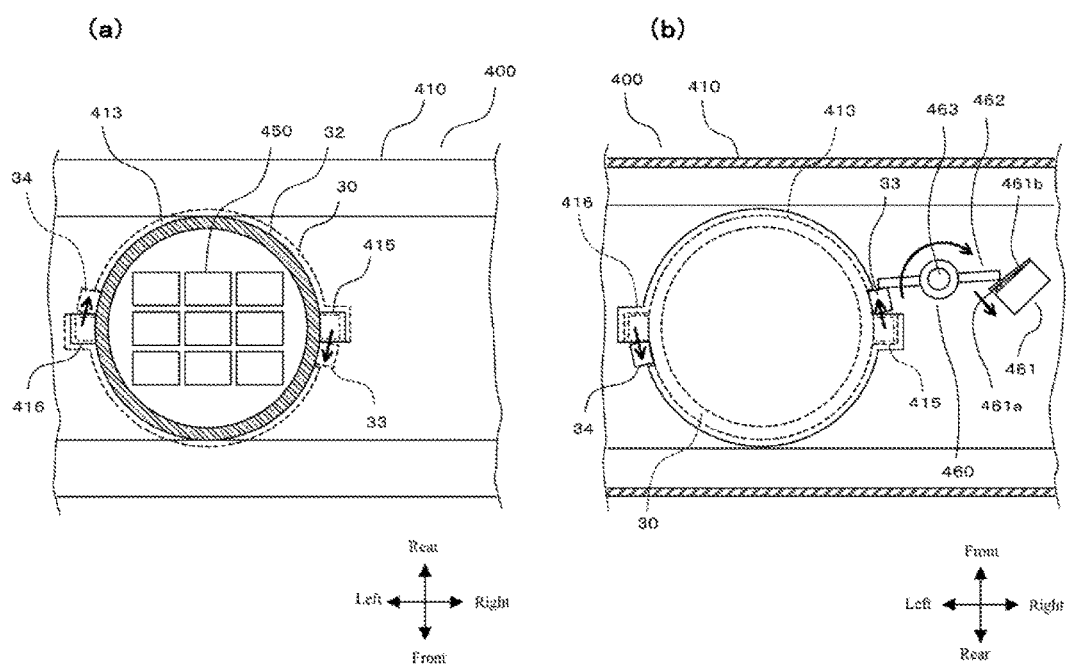
FIG. 8 is a diagram illustrating connection of an induction pipe to an ozone supply apparatus and connection detection through a pipe detection part according to embodiments.

Next, by referring to FIG. 8, connection of the induction pipe 30 to the ozone supply apparatus 20 and connection detection through the pipe detection part 460 are described.

When the induction pipe 30 is connected with the ozone supply apparatus 20, as shown in FIG. 8(a), the connecting part 32 of the induction pipe 30 is inserted into the inserting port part 413 in such a way that the right claw part 33 and the left claw part 34 are inserted into the right inserting concave part 415 and the left inserting concave part 416, respectively. Then, when the induction pipe 30 rotates to the right viewed from above, the right claw part 33 and the left claw part 34 move to the inner side of the upper surface of the shell body 410 through the right opening part 415a and the left opening part 416a, respectively, to clamp with the upper surface of the shell body 410. Thus, the induction pipe 30 does not escape from above.

In this way, the induction pipe 30 is connected with the ozone supply apparatus 20. As shown in FIG. 8(b), when the right claw part 33 moves to the inner side of the upper surface of the shell body 410, one end side of the relay rod 462 is pressed by the right claw part 33. The relay rod 462 rotates to press a rod part 461b by the other end side of the relay rod 462 such that a switch part 461a is pressed by the pressed rod part 461b. Thus, the detection switch 461 detects that the induction pipe 30 has been installed on the inserting port part 413.

It should be noted that when the induction pipe 30 is removed from the inserting port part 413, the rod part 461b rotates the relay rod 462 through itself elasticity while returning to an initial position. Thus, the pipe detection switch 461 detects that the induction pipe 30 has been removed from the inserting port part 413.

Figure 9:
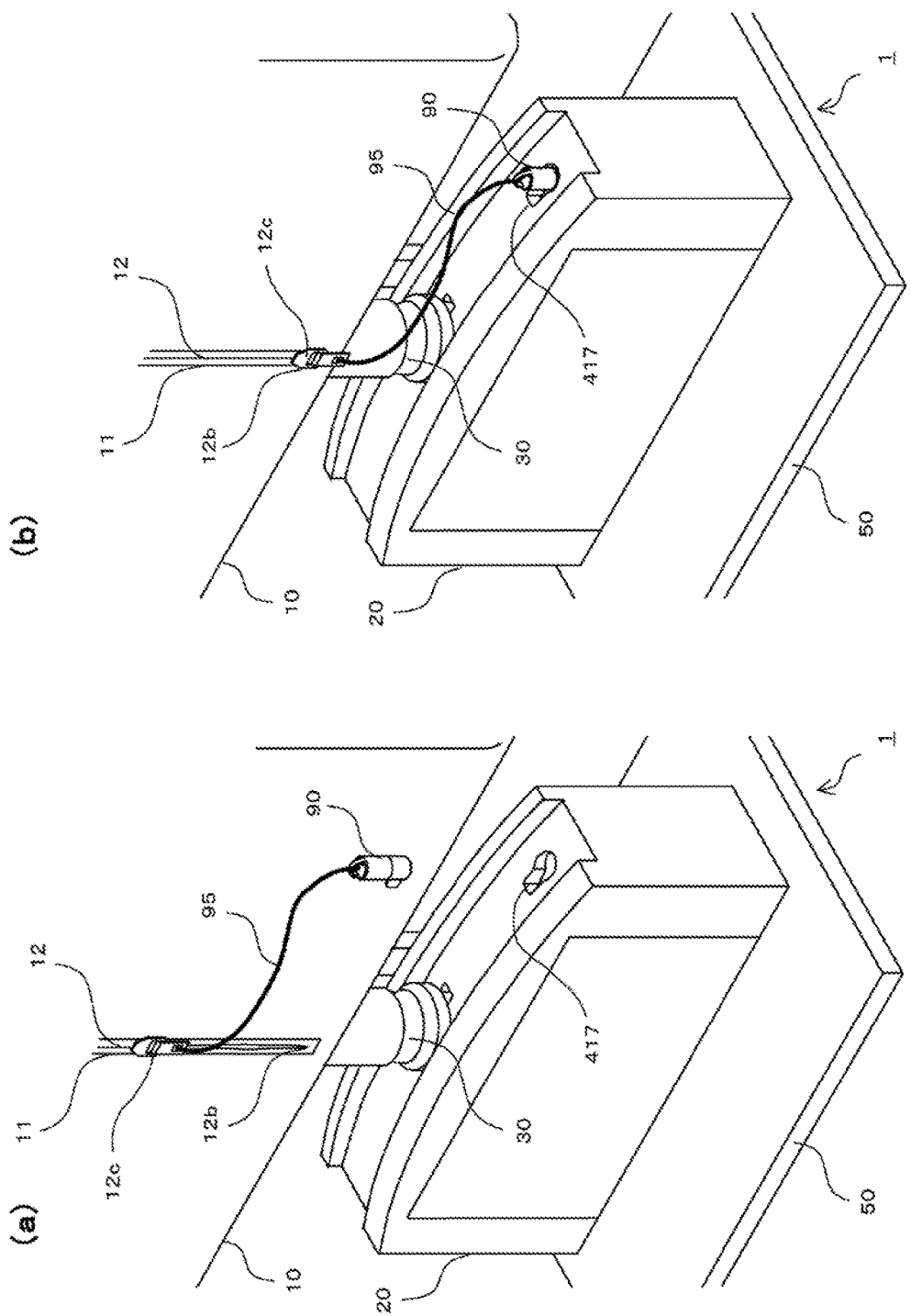
FIG. 9 is a diagram illustrating a detection of a lock detection part that a throwing inlet of a bag body has been locked by a zipper according to embodiments.
Figure 10:
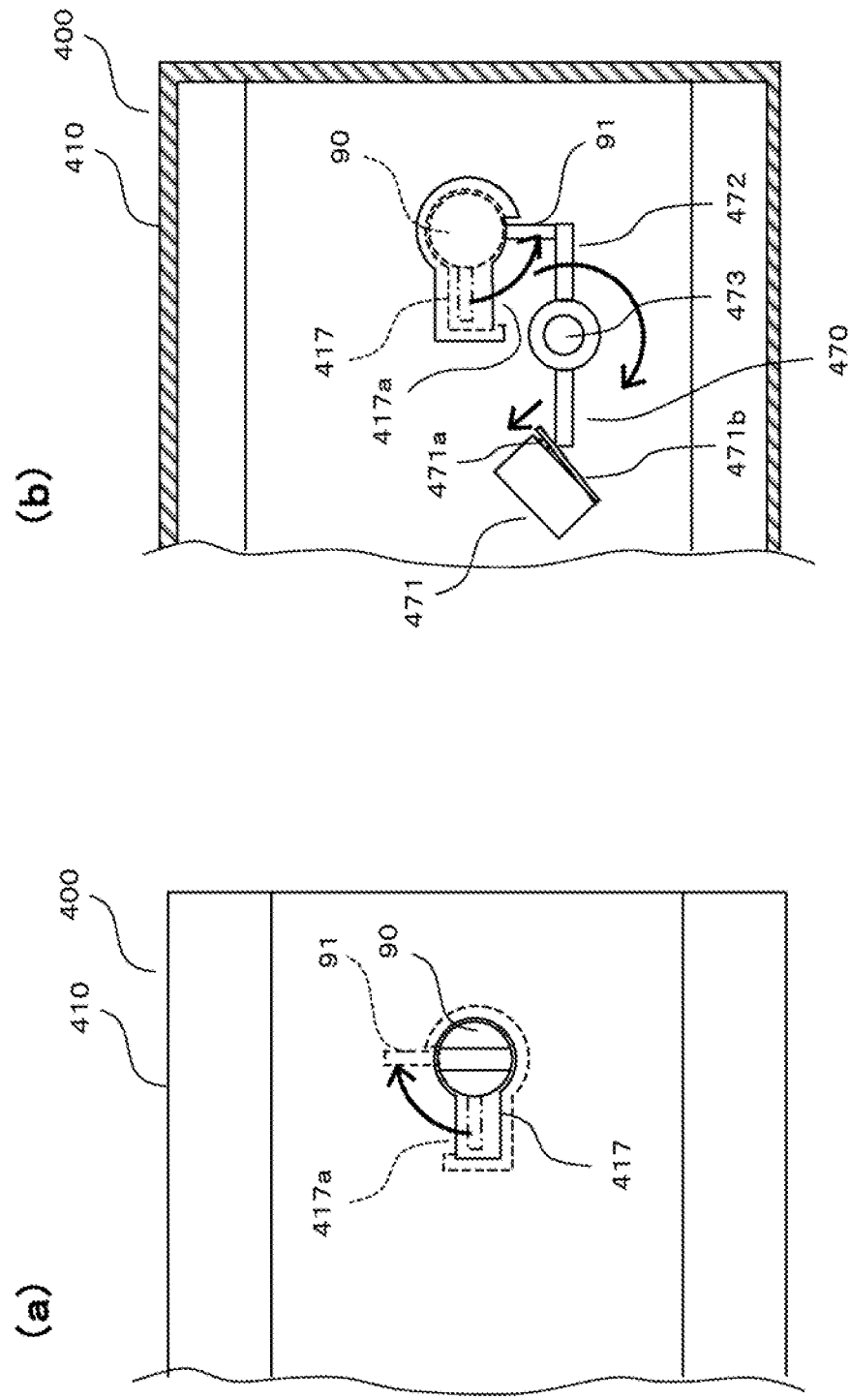
FIG. 10 is a diagram illustrating a detection of a lock detection part that a throwing inlet of a bag body has been locked by a zipper according to embodiments.

Next, by referring to FIGS. 9 to 10, a detection of a lock detection part 470 that a throwing inlet 11 of a bag body 10 has been locked by a zipper 12 is described.

A connecting rope 95 for connecting the detection lock 90 and the slider 12c has a length that the detection lock 90 arrives at the lock inserting concave part 417 when the zipper 12 is locked near the end part 12b. Therefore, as shown in FIG. 9(a), when the slider 12c is not located near the end part 12b, the detection lock 90 fails to reach the lock inserting concave part 417 and the user cannot insert the detection lock 90 into the lock inserting concave part 417. That is, at least in a state that the zipper 12 is completely opened, the detection lock 90 fails to reach the lock inserting concave part 417. On the other hand, as shown in FIG. 9(b), in a state that the zipper 12 is completely closed, the detection lock 90 can reach the lock inserting concave part 417 and is inserted into the lock inserting concave part 417.

When the user locks the throwing inlet 11 completely through the zipper 12, as shown in FIG. 10(a), the detection lock 90 is inserted into the lock inserting concave part 417 and is rotates to the right viewed from above. As shown in FIG. 10(b), the protruding part 91 of the detection lock 90 passes through the opening part 417a to move to the inner side of the upper surface of the shell body 410. One end side of the relay rod 472 is pressed through the moved protruding part 91. The relay rod 472 rotates to press the rod part 471b by the other end side thereof such that the switch part 471a is pressed by the pressed rod part 471b. Thus, the detection switch 471 detects that the detection lock 90 has been inserted into the lock inserting concave part 417, i.e., detects that the throwing inlet 11 of the bag body 10 has been locked by the zipper 12.

It should be noted that when the detection lock 90 is removed from the lock inserting concave part 417, the rod part 471b rotates the relay rod 472 through itself elasticity while returning to an initial position. Thus, the detection switch 471 detects that the detection lock 90 is removed from the lock inserting concave part 417.

Next, a structure of the fragrance supply unit 80 is described in detailed.

Figure 11:
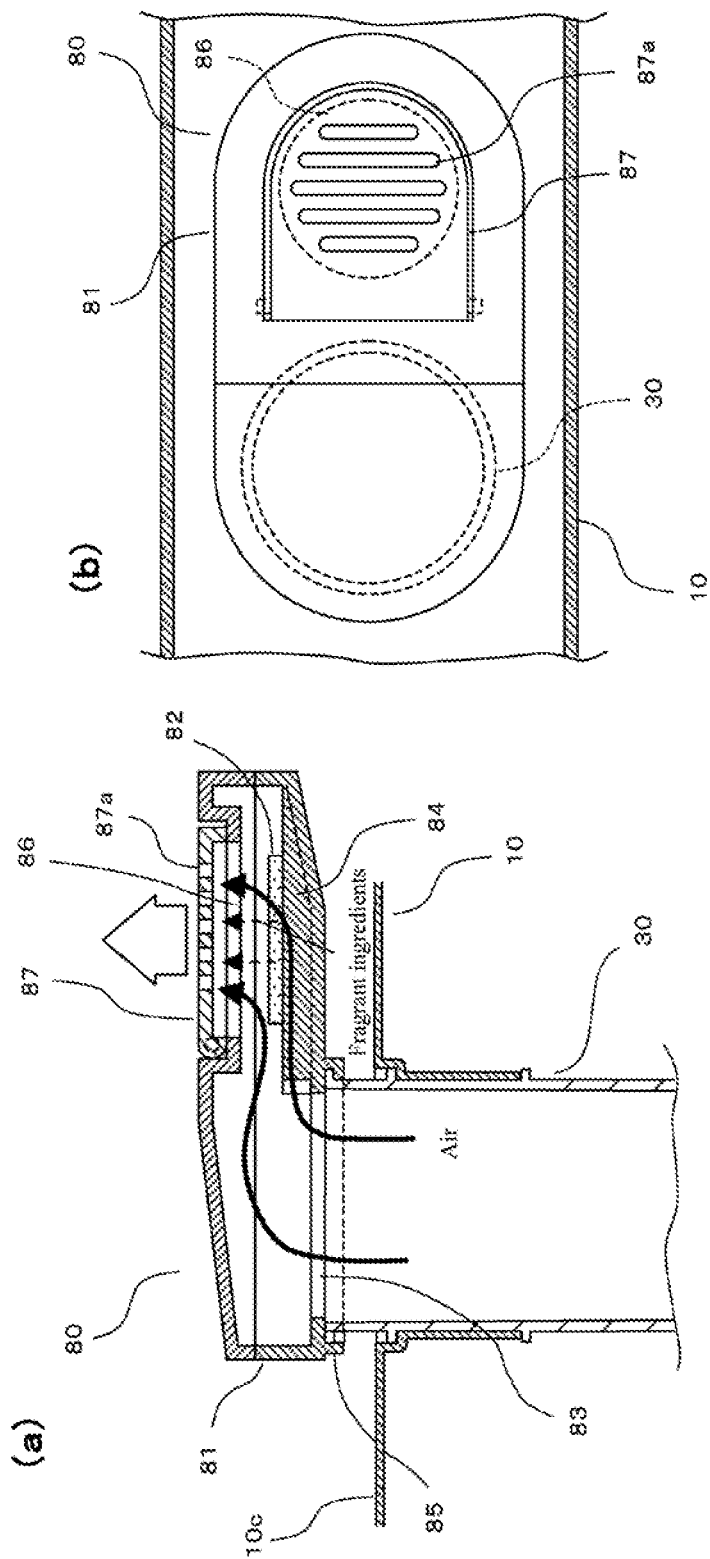
FIG. 11 is a structural diagram illustrating a fragrance supply unit according to embodiments.

FIG. 11 is a structural diagram illustrating a fragrance supply unit 80. FIGS. 11(a) and (b) are a longitudinal section view and a transverse section view illustrating a central part of a lower part of a bag body 10, respectively, in a state that a fragrance supply unit 80 is installed on an induction pipe 30.

The fragrance supply unit 80 includes a box-shaped accommodating box 81 which has an oval when overlooked, and a fragrant body 82 accommodated in the accommodating box 81.

An air suction port 83 and a loading part 84 adjacent to the air suction port 83 and composed of a plurality of ribs extending in a long edge direction are disposed at a bottom surface of the accommodating box 81. The fragrant body 82 is disposed above the loading part 84. In addition, at the bottom surface of the accommodating box 81, a cylindrical connecting port 85 is formed in a manner of encircling the air suction port 83.

At an upper surface of the accommodating box 81, an opening part 86 is formed directly above the loading part 84. The opening part 86 is covered by a cover part 87 with a plurality of vent holes 87a in an openable and closable manner. The fragrant body 82 is formed by porous material such as material which can be immersed in a liquid flavoring agent. The user opens the cover part 87 and arranges the fragrant body 82 into the accommodating box 81 from the opening part 86.

Next, a structure of the control unit 900 is described.

Figure 12:
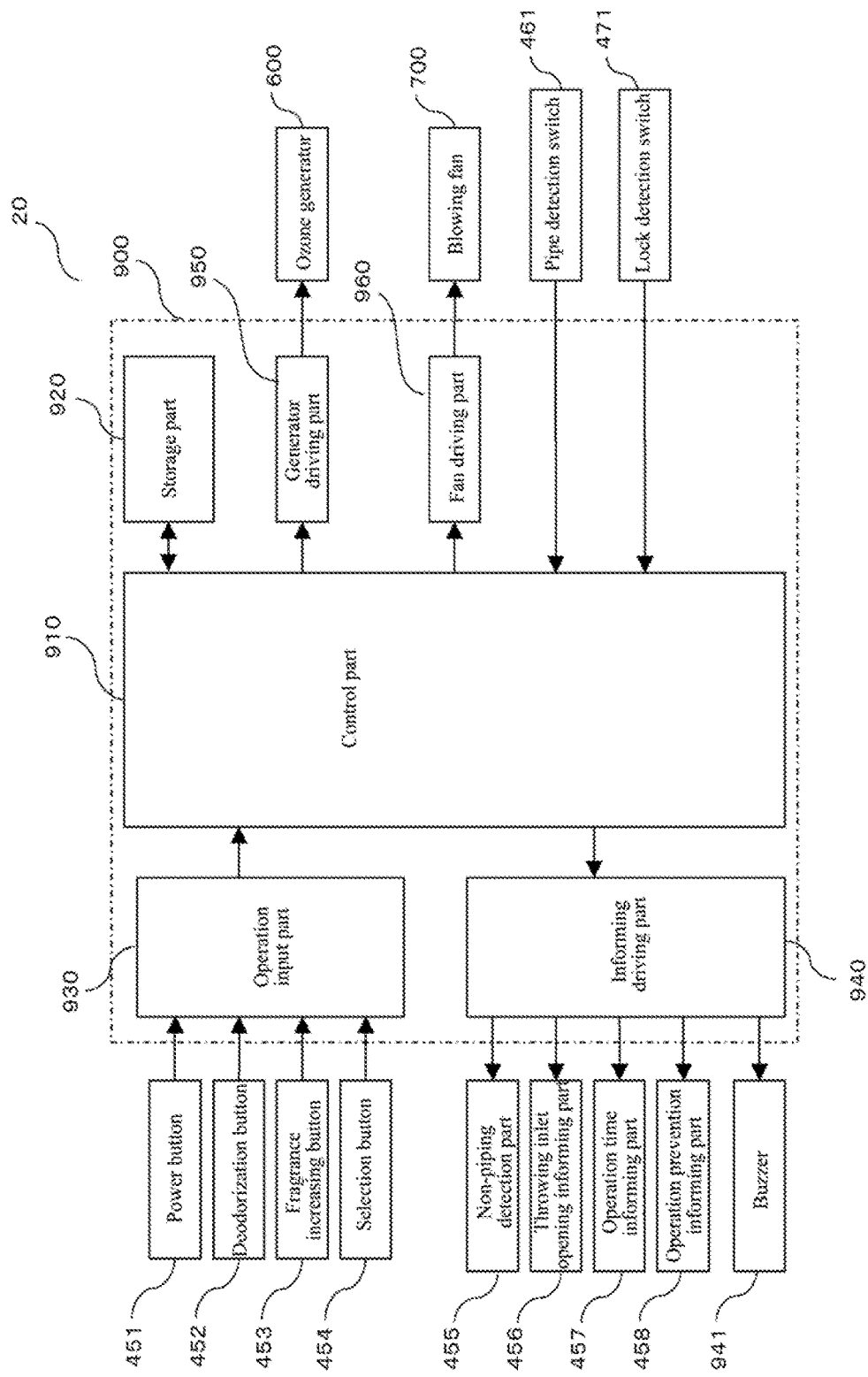
FIG. 12 is a block diagram illustrating a structure of a control unit of an ozone supply apparatus according to embodiments.

FIG. 12 is a block diagram illustrating a structure of a control unit 900 of an ozone supply apparatus 20. The control unit 900 includes: a control part 910, a storage part 920, an operation input part 930, an informing driving part 940, a generator driving part 950 and a fan driving part 960.

The storage part 920 includes memories such as an EEPROM and a RAM. The storage part 920 stores procedures for executing deodorization operation, fragrance increasing operation for example. In addition, the storage part 920 stores various parameters and control marks for the execution of the procedures.

The operation input part 930 outputs an input signal corresponding to the power button 451, the deodorization button 452, the fragrance increasing button 453 and the selection button 454 operated by the user to the control part 910. The informing driving part 940 drives the non-piping informing part 455, the throwing inlet opening informing part 456, the operation time informing part 457, the operation prevention informing part 458 and a buzzer 941 according to a control signal from the control part 910. The generator driving part 950 drives the ozone generator 600 according to a control signal from the control part 910. The fan driving part 960 drives the blowing fan 700 according to a control signal from the control part 910.

When the pipe detection switch 461 detects that the induction pipe 30 is installed on the ozone supply apparatus 20, the detection signal corresponding thereto is outputted to the control part 910. When the lock detection switch 471 detects that the detection lock 90 is installed on the lock inserting concave part 417, i.e., detects that the throwing inlet 11 of the bag body 10 is locked by the zipper 12, the detection signal corresponding thereto is outputted to the control part 910.

The control part 910 controls, for example, the informing driving part 940, the generator driving part 950, the fan driving part 960 for example according to signals from the operation input part 930, the pipe detection switch 461, the lock detection switch 471 in accordance with the procedures stored in the storage part 920.

Next, deodorization operation and fragrance increasing operation of the clothing deodorizing device 1 are described.

Under a condition of performing deodorization operation, the user accommodates the clothing hanged on the clothes hanger H inside the bag body 10 hanged on the bag body holding part 70. At this moment, as shown in FIG. 3(*b*), in the bag body 10, the clothes hanger H is hanged on a second holding part 121 of the clothes hanger holding part 42. In this way, in the bag body 10, the clothing is hanged by the clothes hanger holding part 42. The user presses the deodorization button 452 after selecting operation time through the selection button 454 at the operation part 450 of the ozone supply apparatus 20.

When deodorization operation is started, outside air is taken into the air suction pipe 810 from the air suction port 418, and removes dust and ozone included in the air through the dust filter 820 and the ozone removing filter 830 inside the air suction pipe 810. The air without dust and ozone is delivered into the vent pipe 500 through the blowing fan 700 (with reference to an arrow in FIG. 7(*b*)). The air flowing through the vent pipe 500 is mixed with the ozone generated by the ozone generator 600 when passing through the ozone generator 600. In this way, air containing the ozone arrives at the exhaust port 414 through the vent pipe 500 and is exhausted from the exhaust port 414 (with reference to an arrow in FIG. 7(*a*)).

The air exhausted from the ozone supply apparatus 20 and including the ozone is leaded into the bag body 10 through the induction pipe 30. As shown by an arrow in FIG. 1(*a*), the air leaded into the bag body 10 and including the ozone is in contact with the clothing in the bag body 10 from bottom to top while flowing. The clothing is deodorized through a deodorization effect of the ozone contained in the air.

It should be noted that in the present embodiment, the rotating speed of the blowing fan 700 during the deodorization operation is set in such a manner that air displacement exhausted from the bag body 10 is less than air suction amount sucked into the bag body 10. Thus, when the air containing the ozone is introduced into the bag body 10, the bag body 10 is expanded, and the air pressure inside the bag body 10 is increased. Since the ozone is easy to soak the clothing through the increasing pressure, a deodorization effect of the clothing is enhanced.

The air containing a reduced ozone concentration due to deodorization for the clothing is exhausted from the bag body 10 through the exhaust part 41 above the bag body 10 as shown by a dotted arrow in FIG. 1(*a*). Ozone is removed from deodorized air through the ozone removing filter 300 when the deodorized air passes through the exhaust part 41. Thus, the concentration of the ozone in the air exhausted from the bag body 10 is further reduced.

Next, under a condition of performing fragrance increasing operation, the user accommodates the clothing into the bag body 10 hanged on the bag body holding part 70, and as shown in FIG. 11, in the bag body 10, the fragrance supply unit 80 provided with the fragrant body 82 is installed on the induction pipe 30. The user presses the fragrance increasing button 453 of the operation part 450 of the ozone supply apparatus 20.

When the fragrance increasing operation is started, as shown in FIG. 11(*a*), the air exhausted from the induction pipe 30 is introduced into the accommodating box 81 from the air suction port 83*a*. When the introduced air passes through the fragrant body 82, fragrant ingredients included in the fragrant body 82 volatilize and are mixed into the air. The air containing the fragrant ingredients is discharged into the bag body 10 through the opening part 86 and the vent hole 87*a*.

The air containing the fragrant ingredients flows from bottom to top in the bag body 10, and is exhausted from the exhaust part 41 to an outside of the bag body 10. The fragrant ingredients are absorbed to the clothing accommodated in the bag body 10.

In addition, under a condition that the amount of odour ingredients attached to the clothing is relatively large but the time of performing the deodorization operation is relatively short, after the deodorization operation, a condition that the odour ingredients may remain in the air in the bag body 10 may occur. In this case, during a period from the end of the deodorization operation to the removal of the clothing from the bag body 10, the odour may be reabsorbed to the deodorized clothing.

Therefore, in the present embodiment, after the deodorization operation, reabsorption preventing operation is performed for preventing the odour from reabsorbing to the clothing. In addition, the deodorization operation is equivalent to the first operation of the present disclosure, and the reabsorption preventing operation is equivalent to the second operation of the present disclosure.

In the reabsorption preventing operation, the blowing fan 700 is intermittently operated for a specified operation time, such as 30 minutes. For example, the blowing fan 700 repeatedly performs an operation action of 1-minute energization to 15-second deenergization. At this moment, the ozone generator 600 is in a stopped status.

Figure 13:
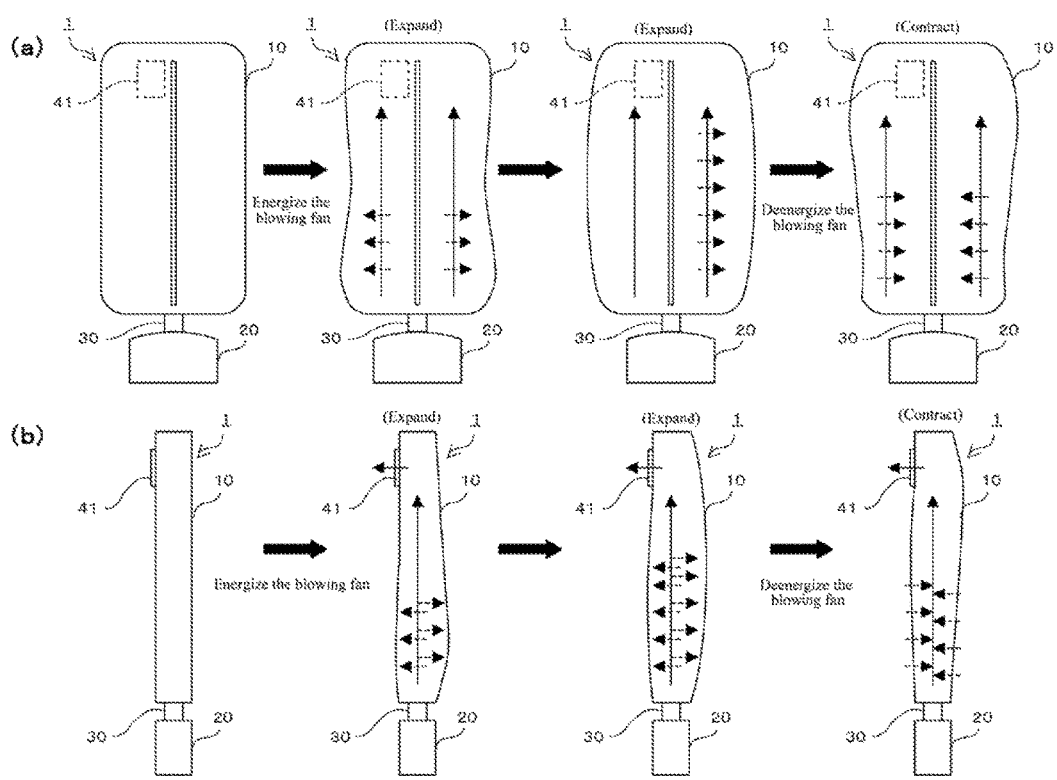
FIG. 13 is a schematic diagram illustrating a state of a clothing deodorizing device when a blowing fan performs intermittent operation during reabsorption preventing operation according to embodiments.

FIG. 13 is a diagram schematically illustrating a state of a clothing deodorizing device 1 when the blowing fan 700 performs intermittent operation during reabsorption preventing operation. FIG. 13(*a*) shows a state of the clothing deodorizing device 1 when observed from a front side. FIG. 13(*b*) shows a state of the clothing deodorizing device 1 when observed from a side.

When the blowing fan 700 is energized, air is introduced into the bag body 10. At this moment, since air delivery amount of the blowing fan 700 is greater than the air displacement from the bag body 10, as shown in FIG. 13, the bag body 10 is expanded. Then, when the blowing fan 700 is deenergized, since air supply is stopped, the bag body 10 is contracted. In this way, through intermittent operation of the blowing fan 700, the bag body 10 is repeatedly expanded and contracted. Thus, relative to the clothing in the bag body 10, the air not only flows from bottom to top as a solid arrow, and can also flow to a front-rear direction and a left-right direction as a dotted arrow. Thus, since the air can effectively circulated around the clothing in the bag body 10, i.e., the clothing in the bag body 10 can be ventilated, the odour ingredients to be attached to the clothing can be effectively away from the clothing, and discharged to the outside.

Figure 14:
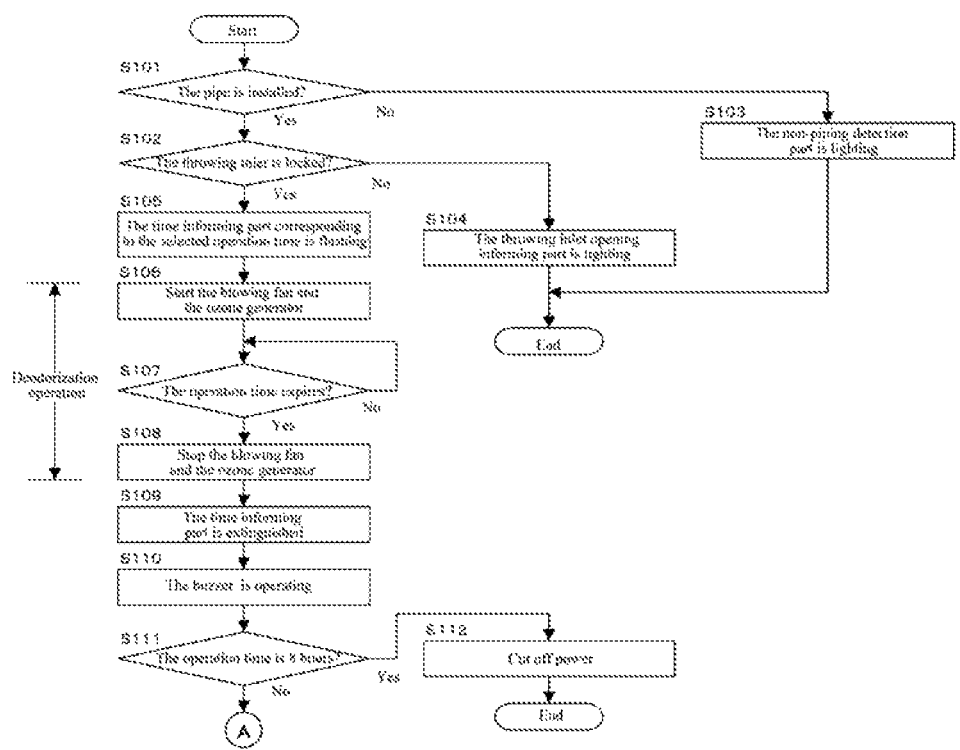
FIG. 14 is a flow chart illustrating a series of control treatments from deodorization operation to reabsorption preventing operation according to embodiments.
Figure 15:
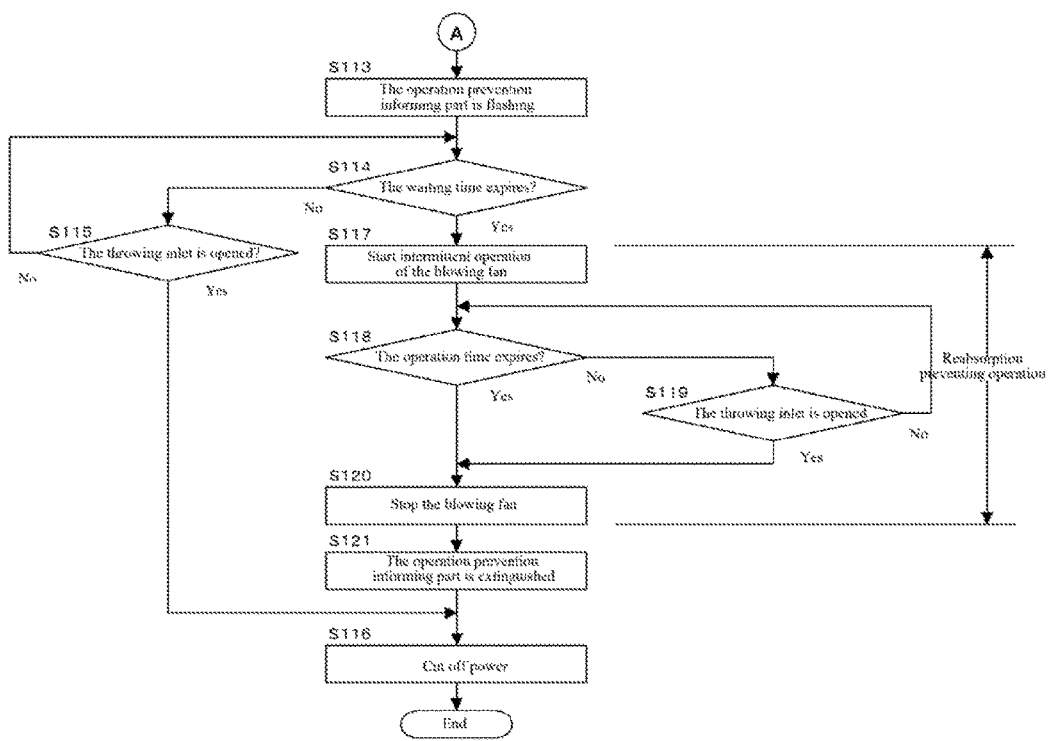
FIG. 15 is a flow chart illustrating a series of control treatments from deodorization operation to reabsorption preventing operation according to embodiments.

FIGS. 14 and 15 are flow charts illustrating a series of control treatments from deodorization operation to reabsorption preventing operation. Control actions of the deodorization operation and the reabsorption preventing operation are described below according to the flow charts of FIGS. 14 and 15.

When the deodorization button 452 is pressed after a desired operation time is selected from the four operation times through the selection button 454, the control treatment is started.

The control part 910 judges whether the induction pipe 30 has been installed on the inserting port part 413 (S101) according to a detection signal from the pipe detection switch 461. In addition, the control part 910 judges whether the throwing inlet 11 of the bag body 10 is locked (S102) according to a detection signal from the lock detection switch 471.

When the deodorization button 452 is pressed in a state that the induction pipe 30 is not installed on the ozone supply apparatus 20, the control part 910 judges that the induction pipe 30 is not installed on the ozone supply apparatus 20 (S101: No), and controls the informing driving part 940, so that the non-piping informing part 455 is lighting (S103). Then, the control part 910 enables the blowing fan 700 and the ozone generator 600 not to operate, and stops the control treatment. In addition, when the deodorization button 452 is pressed in a state that the throwing inlet 11 of the bag body 10 is locked, the control part 910 judges that the throwing inlet 11 is not locked (S102: No), and controls the informing driving part 940, so that the throwing inlet opening informing part 456 is lighting (S104) and stops the control treatment.

On the other hand, under a condition that the introduction pipe 30 has been installed on the inserting port part 413 and the throwing inlet 11 of the bag body 10 is locked (S101: Yes and S102: Yes), the control part 910 controls the informing driving part 940, to enable the time informing part corresponding to the operation time selected by the operation time informing part 457 to flash (S105). The deodorization operation is started, and the control part 910 controls the fan driving part 960 and the generator driving part 950 to start the blowing fan 700 and the ozone generator 600 (S106).

Then, the control part 910 judges whether the operation time expires (S107). When the operation time expires (S107: Yes), the control part 910 stops the blowing fan 700, and stops the ozone generator 600 (S108). Thus, the deodorization operation is ended.

It should be noted that under a condition that the control part 910 stops the ozone generator 600 and the blowing fan 700, the ozone generator 600 is stopped first, and then after a specified time, e.g., 30 seconds, the blowing fan 700 is stopped. So, air without ozone is introduced into the bag body 10 and air containing ozone is extruded from the bag body 10 by the air without ozone, the air containing ozone is inhibited to residue in the bag body 10 at the end of deodorization operation.

The control part 910 extinguishes the flashing time informing part on the operation time informing part 457 (S109). Then, the control part 910 controls the informing driving part 940 that shall inform the end of the deodorization operation to enable the buzzer 941 to operate (S110).

Next, the control part 910 judges whether the selected operation time is 8 hours (S111). Under a condition that the operation time of the deodorization operation is 8 hours (S111: Yes), even if the amount of odour ingredients are attached to the clothing, since the operation time is relatively long, the odour ingredients separated from the clothing can also be sufficiently decomposed through the ozone. Therefore, it can be considered that the odour ingredients hardly remain in the bag body 10 at the end of 8 hours of deodorization operation. Therefore, in this case, the control part 910 does not perform the reabsorption preventing operation, and cuts off a power supply of the ozone supply apparatus 20 (S112).

On the other hand, under a condition that the operation time of the deodorization operation is not 8 hours (S111: No), i.e., under a condition that the operation time is 0.5 hour, 2 hours and 4 hours, the odour ingredients separated from the clothing may not be sufficiently decomposed through the ozone, and may residue in the bag body 10. Therefore, in this case, the control part 910 shall initiate the reabsorption preventing operation, and firstly controls the informing driving part 940 to enable the operation prevention informing part 458 to flash (S113). Next, the control part 910 judges whether a specified waiting time, such as 30 seconds, elapses from the end of the deodorization operation (S114). Then, until the waiting time expires, the control part 910 judges whether the throwing inlet 11 of the bag body 10 is opened (S115) according to a detection signal from the lock detection switch 471.

Under a condition that the user immediately takes out the clothing from the bag body 10 at the end of the deodorization operation, the throwing inlet 11 is opened before the waiting time expires. In this case (S115: Yes), the control part 910 does not perform the reabsorption preventing operation, and cuts off a power supply of the ozone supply apparatus 20 (S116).

On the other hand, when the waiting time elapses in a state that the throwing inlet 11 is not opened (S114: Yes), the control part 910 begins to perform the reabsorption preventing operation. It should be noted that during the waiting time, the air leaks from the bag body 10, and the bag body 10 is contracted to return to a state before the deodorization operation.

The control part 910 controls the fan driving part 960 and starts the intermittent operation of the blowing fan 700 (S117).

Then, the control part 910 judges whether a preset operation time, such as 30 minutes, of the reabsorption preventing operation elapses (S118). In addition, the control part 910 judges whether the throwing inlet 11 is opened (S119). It should be noted that the operation time of the reabsorption preventing operation can also be selected from a plurality of operation times by the user as the operation time of the deodorization operation.

When the throwing inlet 11 is opened when the operation time expires (S118: Yes) or before the operation time expires (S119: Yes), the control part 910 stops the blowing fan 700 (S120). Thus, the reabsorption preventing operation is ended.

The control part 910 extinguishes the operation prevention informing part 458 (S121), and then, cuts off the power supply of the ozone supply apparatus 20 (S116).

<Effects of Present Embodiment>

The present embodiment has the following effects.

(1) Since the reabsorption preventing operation is performed through the operation of the blowing fan 700 at the end of the deodorization operation to generate flow of the air in the bag body 10, the odour can be prevented from reabsorbing to the clothing in the bag body 10. Moreover, the blowing fan 700 is intermittently operated, the bag body 10 is repeatedly expanded and contracted, and the air in the bag body 10 not only flows from bottom to top, but also flows in the front-rear direction and the left-right direction. Therefore, the odour ingredients can be effectively away from the clothing in the bag body 10 and are discharged to the outside.

(2) Since the bag body 10 is repeatedly expanded and contracted during the reabsorption preventing operation, the user can immediately know that the deodorization operation is ended according to a tendency of the bag body 10 distinctive from a tendency during the deodorization operation even without viewing the operation part 450. It should be noted that the user can also know that the deodorization operation is ended by extinguishing the operation time informing part 457 and flashing the operation prevention informing part 458.

(3) Since the blowing fan 700 is intermittently operated, power consumption can be reduced compared with a condition of continuous operation of the blowing fan 700.

(4) Since the reabsorption preventing operation is ended when the throwing inlet 11 of the bag body 10 is opened during performing the reabsorption preventing operation, the reabsorption preventing operation after the clothing are taken from the bag body 10 can be prevented, and power waste can be prevented.

(5) Since the reabsorption preventing operation is not performed under a condition that the odour ingredients are considered to hardly remain after the deodorization operation is performed for a longer time, power waste can be prevented.

(6) Since during the waiting time is setup before performing the reabsorption preventing operation, the bag body 10 is contracted to return to a state before the deodorization operation, the user can be notified that the deodorization operation is ended according to the state of the bag body 10 before the reabsorption preventing operation is started.

<Changed Embodiment>

Although embodiments and changed embodiments regarding the present disclosure are described above, the present disclosure is not limited to the above-mentioned embodiments. In addition, various changes except the above can also be made to embodiments and changed embodiments of the present disclosure.

For example, in above embodiments, under a condition that the operation time of the deodorization operation is longer, i.e., 8 hours, the reabsorption preventing operation is not performed. However, regardless of the operation time, after deodorization operation is ended, as long as the throwing inlet 11 of the bag body 10 is not opened, the reabsorption preventing operation may be also performed.

In addition, in above embodiments, the waiting time is set between the deodorization operation and the reabsorption preventing operation. However, the waiting time may not be set, and the reabsorption preventing operation is started immediately after the deodorization operation is ended.

In addition, various changes can be properly made to embodiments of the present disclosure within a scope of technical concepts of claims.

What is claimed is:

1. A clothing treatment device, comprising:
    a bag body configured to accommodate clothing;
    an ozone supply part comprising an ozone generator and a blowing fan, wherein the ozone generator is configured to generate ozone, and the blowing fan is configured to deliver the ozone generated by the ozone generator into the bag body by airflow; and
    a control part configured to perform a second operation which enables the blowing fan to operate intermittently after performing a first operation which enables the ozone generator and the blowing fan to operate.

2. The clothing treatment device according to claim 1, further comprising a detection part configured to detect whether a clothing throwing inlet disposed at the bag body is opened;
    wherein the control part is further configured to end the second operation in response to determining that the second operation is performed for a specified time and the detection part detects that the throwing inlet is opened before the specified time expires.

3. The clothing treatment device according to claim 1, further comprising an operation part configured to select operation time of the first operation from a first time and a second time longer than the first time;
    wherein the control part is further configured to perform the second operation after the first operation is performed for the first time, and not to perform the second operation after the first operation is performed for the second time.

4. The clothing treatment device according to claim 1, wherein the control part is further configured to start the second operation after a specified waiting time from an end of the first operation.

5. The clothing treatment device according to claim 2, further comprising an operation part configured to select operation time of the first operation from a first time and a second time longer than the first time;
    wherein the control part is further configured to perform the second operation after the first operation is performed for the first time, and not to perform the second operation after the first operation is performed for the second time.

6. The clothing treatment device according to claim 2, wherein the control part is further configured to start the second operation after a specified waiting time from an end of the first operation.

7. The clothing treatment device according to claim 3, wherein the control part is further configured to start the second operation after a specified waiting time from an end of the first operation.

* * * * *